United States Patent
Kavteladze

(12) 
(10) Patent No.: US 10,052,069 B2
(45) Date of Patent: Aug. 21, 2018

(54) DEVICE FOR MEASUREMENT OF PRESSURE AND FOR ADMINISTRATION OF DRUGS TO AN ANEURYSM IN A BLOOD VESSEL

(71) Applicant: Zaza Alexandrovich Kavteladze, Moscow (RU)

(72) Inventor: Zaza Alexandrovich Kavteladze, Moscow (RU)

(*) Notice: Subject to any disclaimer, the term of this patent is extended or adjusted under 35 U.S.C. 154(b) by 313 days.

(21) Appl. No.: 14/689,986

(22) Filed: Apr. 17, 2015

(65) Prior Publication Data
US 2016/0038085 A1 Feb. 11, 2016

(30) Foreign Application Priority Data
Aug. 6, 2014 (RU) ................. 2014132234

(51) Int. Cl.
*A61B 5/02* (2006.01)
*A61B 5/00* (2006.01)
(Continued)

(52) U.S. Cl.
CPC ........ *A61B 5/6857* (2013.01); *A61B 5/02014* (2013.01); *A61B 5/0215* (2013.01);
(Continued)

(58) Field of Classification Search
CPC ....... A61B 5/02; A61B 5/2015; A61B 5/6862; A61B 5/02014; A61B 5/0215;
(Continued)

(56) References Cited

U.S. PATENT DOCUMENTS 5,037,403 A  8/1991 Garcia
5,716,365 A  2/1998 Goicoechea et al.
(Continued)

FOREIGN PATENT DOCUMENTS

EP  2910184 A1  8/2015
RU  2521833 C2  10/2012
(Continued)

OTHER PUBLICATIONS

Dias NV et al., "Direct intra-aneurysm sac pressure measurement using tip-pressure sensor: in vivo and in vitro evaluation", Journal of vascular-surgery, 711-6, 2004.
(Continued)

*Primary Examiner* — Jacqueline Cheng
*Assistant Examiner* — Eric Messersmith
(74) *Attorney, Agent, or Firm* — Banner & Witcoff, Ltd.

(57) ABSTRACT

The invention relates to medicine, in particular, to vascular and endovascular surgery, and can be used for assessment of the condition of an isolated space of an aneurysmal sac after implantation of a stent-graft by measuring pressure inside the sac, and for administration of drugs to an aneurysm in a blood vessel as far as necessary. The device for measurement pressure in an isolated space of an aneurysmal sac and for administration of drugs to an aneurysm in a blood vessel is made in the form of a hollow tube. The tube has side apertures and is adapted to change a shape when introduced into an aneurysm, and to fill the entire interior space of the aneurysm at its circumference. The tube is also adapted to be connected to a pressure-measuring sensor through a detachable hollow tube to measure pressure between the vessel wall and the wall of a stent-graft implanted to the blood vessel, and to administer drugs through said detachable hollow rube. The tube is made of a viscoelasticity resorbable material and coiled in a spiral form. The invention allows addressing a plurality of problems: cost saving on production of the device, facilitation of an invasion process, (Continued)

measurement of pressure, administration of drugs, improvement of direct and late results by ensuring thrombosing of an aneurysmal sac.

11 Claims, 2 Drawing Sheets

(51) Int. Cl.
*A61B 5/0215* (2006.01)
*A61F 2/07* (2013.01)

(52) U.S. Cl.
CPC .......... *A61B 5/4839* (2013.01); *A61B 5/6862* (2013.01); *A61B 2560/04* (2013.01); *A61B 2562/0247* (2013.01); *A61F 2/07* (2013.01)

(58) Field of Classification Search
CPC . A61B 5/6857; A61B 5/4839; A61B 2560/04; A61B 2562/0247; A61F 2/07
See application file for complete search history.

(56) References Cited

U.S. PATENT DOCUMENTS

| 6,669,647 | B2 | | 12/2003 | Letort et al. | |
| 8,398,703 | B2 | * | 3/2013 | Kassab | A61B 17/0057 |
| | | | | | 623/1.15 |
| 2003/0074049 | A1 | * | 4/2003 | Hoganson | A61F 2/07 |
| | | | | | 623/1.13 |
| 2007/0050018 | A1 | | 3/2007 | Wainwright | |
| 2011/0230952 | A1 | * | 9/2011 | Kassab | A61B 17/12022 |
| | | | | | 623/1.11 |
| 2012/0330342 | A1 | | 12/2012 | Jones et al. | |
| 2014/0005714 | A1 | * | 1/2014 | Quick | A61L 31/022 |
| | | | | | 606/200 |
| 2015/0257657 | A1 | | 9/2015 | Kavteladze | |

FOREIGN PATENT DOCUMENTS

| RU | 2012144358 A | 4/2014 |
| WO | 062089 A1 | 4/2014 |
| WO | 2014062089 A1 | 4/2014 |

OTHER PUBLICATIONS

The official journal of the Russian Society of Angiologists and Vascular Surgeon, Angiologoy and Vascular Surgery, vol. 19, appendix, 2', 2013.

\* cited by examiner

DEVICE FOR MEASUREMENT OF PRESSURE AND FOR ADMINISTRATION OF DRUGS TO AN ANEURYSM IN A BLOOD VESSEL

CROSS-REFERENCE TO RELATED APPLICATIONS

This application claims the benefit of priority under 35 U.S.C. § 119(a) of application RU 2014132234, filed Aug. 6, 2014, the contents of which are hereby incorporated by reference in their entirety.

FIELD OF THE INVENTION

The invention relates to medicine, in particular, to vascular and endovascular surgery, and can be used for assessment of the condition of an isolated aneurysmal sac after the implantation of a stent-graft by measuring pressure inside the sac, and for administration of drugs to an aneurysm in a blood vessel as far as necessary.

BACKGROUND OF THE INVENTION

A stent-graft providing internal isolation of an aneurysm in a blood vessel is known (see U.S. Pat. No. 5,716,365, A61F, 1998). A disadvantage of the stent-graft is in impossibility of assessing the condition of an isolated aneurysmal sac after the implantation of the stent-graft (in particular, of measuring of intra-aneurysm sac pressure and administering drugs, as far as necessary).

A device for measurement of pressure and for administration of drugs is known (see U.S. Pat. No. 5,037,403, A61M 25/00, 1991), wherein the device is made in the form of a catheter with side apertures. Said device is the closest technical solution in terms of the problem to be solved.

A disadvantage of the known technical solution is in impossibility of assessing the condition of an isolated space of an aneurysmal sac between the aneurysmal vessel wall and the wall of a stent-graft after the implantation of the latter.

The closest prior art to the present invention is a device for measurement of pressure in an isolated space of an aneurysmal sac, and for administration of drugs to an aneurysm in a blood vessel, the device being made in the form of a nitinol hollow tube with side apertures. The tube is adapted to change a shape when introduced into an aneurysm, and to fill the entire interior space of the aneurysm at its circumference. The tube is also adapted to be connected to a pressure-measuring sensor through a detachable hollow tube to measure pressure between the vessel wall and the wall of a stent-graft implanted to the blood vessel, and to administer drugs through said detachable hollow tube (RU 2521833 C2, A61M 25/00, 2014).

The known technical solution has the following drawbacks:
difficulty of implanting said device;
impossibility of removing the device after using thereof; and
expensiveness and manufacturing complexity since, due to the shape and size of the device assigned during manufacture, such a device can be implanted only to this particular aneurism, and a stent that can be positioned inside such a device also has a strictly defined size.

SUMMARY OF THE INVENTION

The objective of the invention is to eliminate the above disadvantages and to develop a universal device that provides assessment of the condition of an isolated space of an aneurysmal sac by measuring pressure, and provides administration of drugs to the aneurysm in a blood vessel after implantation of a stent-graft.

The objective is addressed by providing a device for measurement of pressure in an isolated space of an aneurysmal sac and for administration of drugs to an aneurysm in a blood vessel, wherein the device is made in the form of a hollow tube. The tube has side apertures and is adapted to change the shape when introduced into an aneurysm, and to fill the entire interior space of the aneurysm at its circumference. The tube is also adapted to be connected to a pressure-measuring sensor through a detachable hollow tube to measure pressure between the vessel wall and the wall of a stent-graft implanted to the blood vessel, and to administer drugs through said detachable hollow tube. The tube is made of viscoelasticity resorbable material and coiled in a spiral form.

BRIEF DESCRIPTION OF THE DRAWINGS

The essence of the invention is explained by figures, wherein:

FIG. 1B shows a tube coiled in a conic shape; and FIG. 1C shows a tube having a barrel-like shape).

DETAILED DESCRIPTION OF THE INVENTION

Figure 1C:
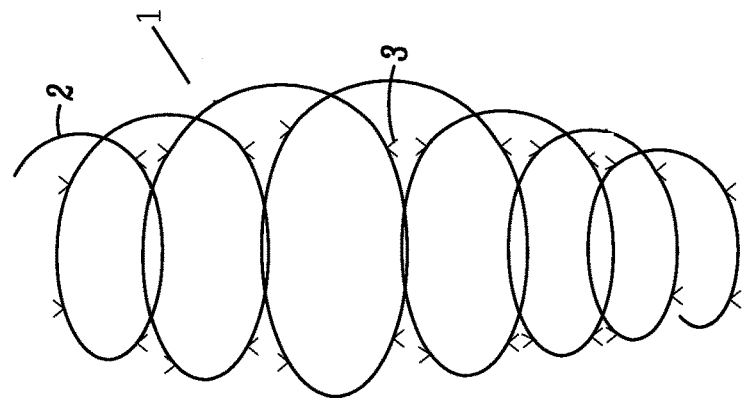
FIGS. 1A-1C show embodiments of the device for measurement of pressure and for administration of drugs before its introduction into a vessel (FIG. 1A shows a tube coiled in a cylindrical shape.
Figure 1B:
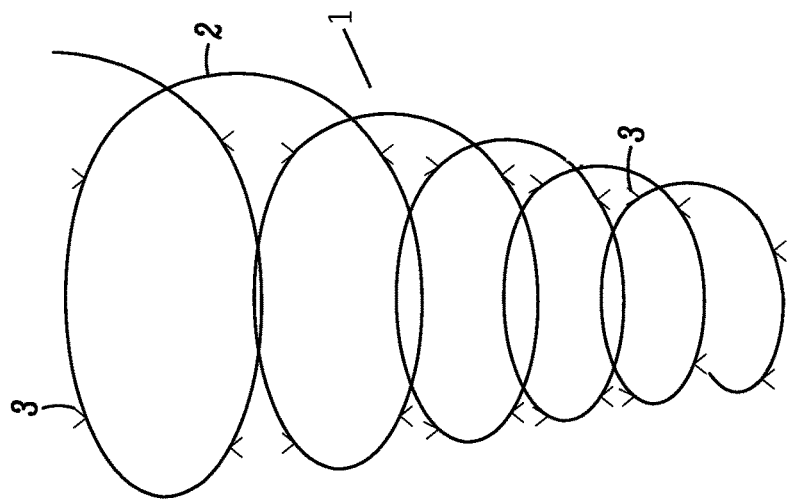
Figure 1A:
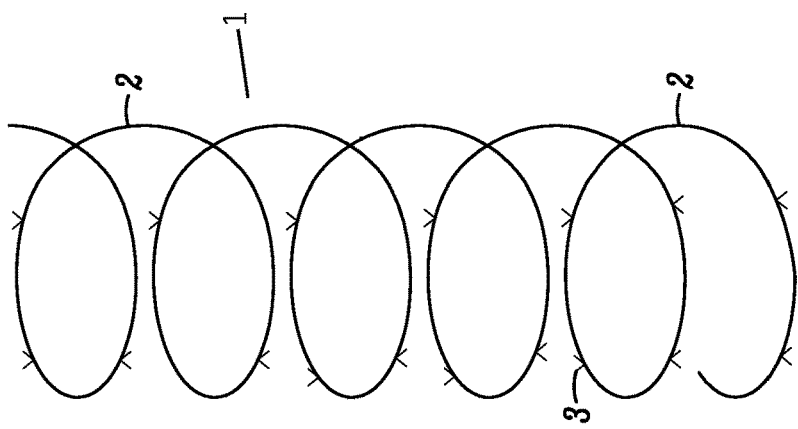

In the claimed invention, device 1 (FIGS. 1A-1C) for measurement of pressure and for administration of drugs is made in the form of a hollow tube 2 with an open or closed (blind) end (not shown) and side apertures 3. Hollow tube 2 is made of viscoelasticity resorbable material, for example, polylactate. Spiral-like coiled tube 2 may be of various shapes (cylindrical, conic, barrel-like, etc.) and is adapted to be connected to a pressure-measuring sensor (not shown) through a detachable hollow tube 4, and to administer drugs through said detachable hollow tube 4.

Figure 2:
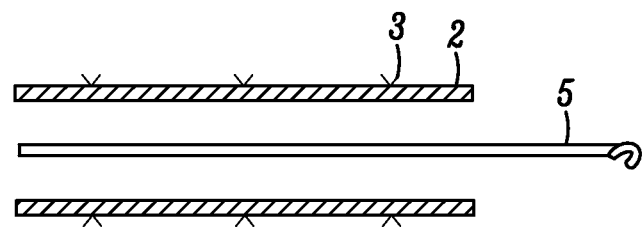
FIG. 2 shows the device before its implantation into an aneurism.
Figure 3:
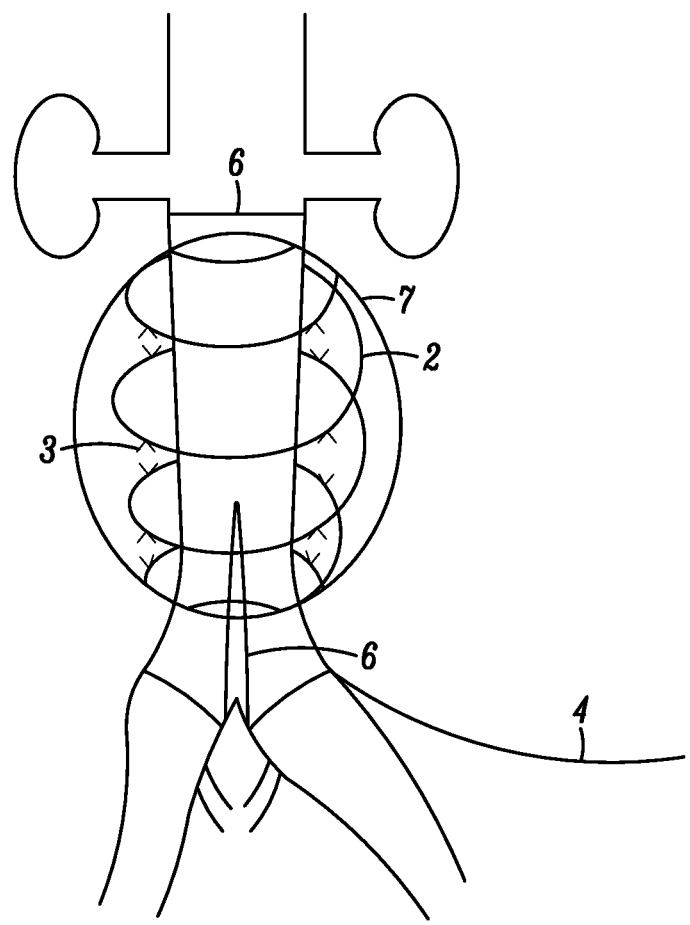
FIG. 3 shows the device disposed in a vessel with a stent-graft positioned therein.

The device is used as follows:

Before introduction the device into the aorta, an aneurysm in a blood vessel is diagnosed. Device 1 is straitened (elongated) by extension provided by the elastic properties of the material and disposed on a guide 5 (FIG. 2). Then, the device is introduced into the aneurism by a known method. Once device 1 enters an aneurismal sac, guide 5 is removed from hollow tube 2. Due to elastic material of the device, hollow tube 2 attempts to resume its original shape and fills the entire space of the aneurism at its circumference. Then, stent-graft 6 is positioned inside spiral-like coiled hollow tube 2 to isolate the aneurysmal sac. Stent-graft 6 is implanted by a known method by positioning stent-graft 6 so that after the implantation thereof, device 1 for measurement of pressure and for administration of drugs to an aneurysm in a blood vessel was between the wall of aneurysm 7 and the wall of stent-graft 6. To assess the condition of the aneurysmal sac after the implantation of stent-graft 6, spiral-like coiled hollow tube 2 is connected to a pressure-measuring sensor (not shown) through detachable hollow tube 4. Using side apertures 3 made in hollow tube 2 the pressure in the isolated aneurysmal sac is measured. If necessary, a drug, for example thrombosing adhesive, is administered through the same detachable hollow tube 4. Then, detachable hollow tube 4 is disconnected from spiral-like coiled tube 2, and the latter is remained in patient's body for a time until its complete resorption.

Thus, the design of the device for measurement of pressure and for administration of drugs in an aneurysm in a blood vessel, made in the form of a spiral-like coiled hollow tube produced from of a viscoelasticity resorbable material allows addressing a plurality of problems: cost saving on production of the device, facilitation of an invasion process, measurement of pressure, administration of drugs, improvement of direct and late results by ensuring thrombosing of an aneurysmal sac.

The invention claimed is:

1. A device for measurement of pressure in an isolated space of an aneurysmal sac between an aneurysmal vessel wall and a wall of the stent-graft and for administration of drugs in said aneurysmal sac, the device, comprising:
   a first hollow tube, having side apertures, the first hollow tube shaped and sized to conform to the interior space of the aneurysmal sac at its circumference when introduced into the aneurysm, wherein the first hollow tube is made of a resorbable material and is coiled in a spiral form, and
   a second hollow tube, wherein the second hollow tube is configured to be removably attached to the first hollow tube and is further configured to be removably attached to a pressure-measuring sensor to measure pressure between the aneurysmal vessel wall and the wall of the stent-graft implanted within the blood vessel,
   wherein the second hollow tube is further configured to allow for administration of drugs through the second hollow tube.

2. The device of claim 1, wherein the first hollow tube coiled in a spiral form has a cylindrical shape.

3. The device of claim 1, wherein the first hollow tube coiled in a spiral form has a conic shape.

4. The device of claim 1, wherein the first hollow tube coiled in a spiral form has a barrel-like shape.

5. The device according to any one of claims 1-4, wherein an end of the first hollow tube is blind.

6. The device of claim 1, wherein the side apertures are configured to be positioned towards the interior of the circumference of the aneurysmal sac.

7. A method for treating an aneurysm, comprising:
   disposing the device of claim 1, in a straightened form on a guide and introducing the device into the aneurysm;
   removing the guide from the first hollow tube, causing it to adopt a coiled shape against a vessel wall of the aneurysm;
   implanting a stent-graft within the aneurysm and within the coiled shape of the first hollow tube;
   connecting the second hollow tube to the first hollow tube, said second hollow tube being configured, via said side apertures of said first hollow tube, for administration of a drug into the aneurysm and for measurement of the pressure in the aneurysm.

8. The method of claim 7, further comprising administering the drug through the second hollow tube and into the aneurysm via the side apertures of the first hollow tube.

9. The method of claim 8, wherein the drug is administered between the vessel wall of the aneurysm and the stent graft that has been implanted within the aneurysm.

10. The method of claim 7, further comprising measuring the pressure in the aneurysm via the side apertures of the first hollow tube.

11. The method of claim 10, wherein the pressure is measured between the vessel wall of the aneurysm and the stent graft that has been implanted within the aneurysm.

* * * * *